United States Patent
Kus et al.

Patent Number: 5,649,962
Date of Patent: Jul. 22, 1997

[54] METHOD AND APPARTAUS FOR TREATING A PORTION OF A SUTURE AND FORMING A SUTURE TIP FOR ATTACHMENT TO A NEEDLE

[75] Inventors: Joseph E. Kus, Ivanhoe, Ill.; Francis D. Colligan, Waterbury, Conn.

[73] Assignee: United States Surgical Corporation, Norwalk, Conn.

[21] Appl. No.: 544,357

[22] Filed: Oct. 17, 1995

Related U.S. Application Data

[62] Division of Ser. No. 319,690, Oct. 7, 1994, Pat. No. 5,507,777.

[51] Int. Cl.$^6$ ................................................. A61B 17/06
[52] U.S. Cl. ...................................... 606/224; 606/223
[58] Field of Search ........................... 606/222, 223, 606/224, 226, 229, 230, 231; 264/145; 427/2.1, 289, 434.2

[56] References Cited

U.S. PATENT DOCUMENTS

| | | |
|---|---|---|
| 2,734,506 | 2/1956 | Nichols et al. . |
| 3,736,646 | 6/1973 | Schmitt et al. . |
| 3,890,975 | 6/1975 | McGregor . |
| 3,980,177 | 9/1976 | McGregor . |
| 4,832,025 | 5/1989 | Coates . |
| 5,007,922 | 4/1991 | Chen et al. . |
| 5,102,418 | 4/1992 | Granger et al. . |
| 5,123,911 | 6/1992 | Granger et al. . |
| 5,156,788 | 10/1992 | Chesterfield et al. . |
| 5,226,912 | 7/1993 | Kaplan et al. ............... 606/224 |
| 5,269,808 | 12/1993 | Proto et al. . |
| 5,280,674 | 1/1994 | Granger et al. ............... 606/224 |

*Primary Examiner*—Michael Buiz
*Assistant Examiner*—Kevin Truong

[57] ABSTRACT

A delimited portion of suture material is immersed into a freezing media, such as liquid nitrogen, until the delimited portion is frozen. The frozen delimited portion is cut to provide a stiffened, non-brooming suture tip suitable for insertion into a needle bore. The cut, frozen suture tip is inserted into a needle and the needle is crimped to attach the suture to the needle. After attachment, the frozen suture tip returns to ambient temperature, reversing the effects of freezing the suture portion so that the suture adjacent the needle is as flexible as the remainder of the suture.

3 Claims, 2 Drawing Sheets

METHOD AND APPARTAUS FOR TREATING A PORTION OF A SUTURE AND FORMING A SUTURE TIP FOR ATTACHMENT TO A NEEDLE

This is a divisional of U.S. application Ser. No. 08/319, 690, filed Oct. 7, 1994, now U.S. Pat. No. 5,507,777.

BACKGROUND

1. Technical Field

The present disclosure relates to a method and apparatus for treating a portion of a multifilament braided suture to prevent the suture portion from brooming. More particularly, the present disclosure relates to tipping and cutting multifilament sutures, especially braided sutures, and to the insertion of the cut, tipped suture into a needle for attachment of the suture to a needle.

2. Background

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acid.

Needle-suture combinations fall into two general classes: standard, or non-detachable, needle attachment and removable, or detachable, needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture (for various suture sizes) are set forth in the *U.S. Pharmacopoeia* ("USP"). As to detachable needles, the USP prescribes individual pull-out forces and average pull-out forces as measured for five needle-suture combinations. The pull-out forces for both standard and removable needle-suture attachment set forth in the USP are hereby incorporated by reference.

One typical method for securing a suture to a needle involves providing a cylindrical recess in the shank end of a needle and securing a suture therein. For example, U.S. Pat. No. 1,558,037 teaches the addition of a cement material to a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665, 216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Insertion of sutures into a hole, recess or tube for attachment to surgical needles presents problems peculiar to suture needle combinations. Braided multifilament sutures in particular are difficult to insert into the very small aperture of a surgical needle; unless modified, they are too limp for the suture tip to be controlled for insertion and they have a tendency to "broom", i.e., the filaments have a tendency to flare out at the cut end so that the diameter of the cut end exceeds the diameter of the needle hole. Various techniques have been employed to modify sutures to overcome the problems of limpness and brooming. One known method employs a tipping agent, which is a material used to coat the suture to stiffen the filaments and adhere them together.

Typically, a suture to be tipped is first placed under tension to reduce slack so that the suture may be maintained in a predetermined position on a frame or rack or other suture holding device. Optionally, the tension may be such as to reduce the diameter of the suture. See, Canadian Patent No. 1,009,532. The suture is then dipped into the tipping solution and allowed to dry while under tension. The sutures are dried, for example, by being warmed in a drying oven at about 225° F. for about 10 minutes. After drying the sutures can be cut and released from tension. The process results in a tipped end on each side of a cut, with the tipping agent adhering the suture filaments to one another to prevent brooming. The tipped end facilitates insertion of the suture end into a needle bore. Where tension has optionally been employed to reduce the suture diameter, release of said tension will allow the suture to expand to its original diameter except at the tipped portion. This can further facilitate insertion of the end into a needle.

Tipping agents may be dissolved in solvents to form dipping solutions. By way of example, Mariotte mixture is a dipping solution comprising nylon dissolved in isopropyl alcohol. Other polymers and solvents may also be used. Gould mixture is a dipping solution comprising nylon dissolved in methanol. At least one major manufacturer of surgical needles recommends use of Mariotte mixture or Gould mixture for tipping sutures. A multitude of other tipping agents, including polymers and solvents, have been proposed. For example McGregor (U.S. Pat. No. 3,890,975) discloses coating the suture with a binding resin or adhesive. The composition may be any non-toxic adhesive composition, either organic, inorganic or a hybrid. Suitable organic materials are such natural products as starch, dextrin, asphalt, animal and vegetable proteins, natural rubber, shellac; semi-synthetic products such as cellulose nitrate and the other cellulosics, polyamides derived from dimer acids, or castor-oil based polyurethanes; and well-known synthetic resins such as vinyl-type addition polymers, both resins and elastomers, polyvinyl acetate, polyvinyl alcohol, acrylics, unsaturated polyesters, butadiene/acrylonitrile, butadiene/styrene, neoprene, butyl rubber, polyisobutylene, and polymers formed by condensation and other step-wise mechanisms, i.e., epoxies, polyurethanes, polysulfide rubbers, and the reaction products of formaldehyde with phenol, resorcinol, urea, and melamine. McGregor states that particularly preferred bonding compositions are epoxide resins and polyester resins.

Schmitt U.S. Pat. No. 3,736,646 discloses that it is known to tip braided sutures by dipping the end of the suture in plastic such as a polymer solution in isopropyl alcohol. Schmitt suggests that for absorbable sutures an absorbable tipping agent is desirable, and proposes that a copolymer of lactic and glycolic acid dissolved in a suitable organic solvent, such as xylene or toluene, be applied to tip the suture.

Nichols U.S. Pat. No. 2,734,506 discloses a dipping solution of polymers of methacrylic acid esters in an organic solvent such as toluene, xylene acetone, ethyl acetate, methyl ethyl ketone, or naphtha.

Shepherd et al. U.S. Pat. No. 3,849,185 discloses the use of an acrylic casting syrup as a tipping agent, the syrup being fully polymerized after being applied to the suture.

In addition, paraffin/hexane solution (10% paraffin) has been used as a suture coating agent as well as Arrochem (TM), a nylon resin plus methanol composition manufactured by Arrochem, Inc. of 201 Westland Farm Road, Mr. Holly, N.C. 28120, and SILASTIC (TM) Medical Adhesive (a silicon elastomer composition manufactured by Dow Corning Co.

U.S. Pat. No. 5,269,808 to Proto et al., discloses a method and apparatus for tipping sutures which provides superior stiffening of the sutures, and which may be employed for both coated and uncoated sutures. The method includes passing selected portions of the suture through a mist of cyanoacrylate tipping agent generated by ultrasonic atomization. The tipping agent quickly cures and the treated portion of the suture may be cut to create a tipped end for insertion into a surgical needle to form a needle suture device.

Another method which has been employed for treating sutures involves melt fusion, as described in U.S. Pat. No. 4,832,025, issued to Coates. The suture is heated to a temperature at least high enough to "melt fuse" a portion of the outer filaments of the suture. According to Coates, such temperature is typically about 260° C. to 300° C. (500° F. to 572° F.). Exposure of synthetic sutures to such extreme temperatures melt fuses the filaments, and the melt fused suture portion stiffens upon cooling. Melting of the filaments has the effect of holding the filaments together when the suture is cut. It also causes stiffening of the suture which facilitates insertion of the suture end into the drilled hole of a needle. However, the melt fusion of suture has significant drawbacks.

Firstly, the melt fusion of filaments weakens the suture, whose tensile strength is degraded in proportion to the extent of melt fusion.

Secondly, melt fusion causes an irreversible change in the filaments which result in permanent stiffening and permanent loss of tensile strength.

Thirdly, with the extreme temperatures disclosed by Coates for melt fusion an inconveniently short heating cycle is required. For example, for a size 3/0 silicone coated polyester suture heated to between 260° C. to 300° C. in a 4 mm. diameter heating tunnel, the heating time is no more than about 3 seconds. Such short heating time makes it difficult to control the process and leads to inconsistencies and variations in the melt fused tipping process.

U.S. Pat. No. 5,156,788 to Chesterfield et al., discloses a method and apparatus for tipping sutures by delimiting a portion of the suture and heating the delimited portion under predetermined time and temperature conditions to reversibly stiffen the delimited portion upon cooling. The cooled, stiffened suture portion is cut to provide a suitably stiffened, non-brooming suture tip for insertion into a needle.

A further consideration pertinent to suture tipping is that sutures are often prepared with lubricant coatings such as absorbable polymers, silicone or fatty acid salts in order to increase lubricity and to improve "tie-down" performance, i.e., the ease of sliding a knot down the suture into place. Such lubricant coatings may be incompatible with the materials and methods currently employed for tipping sutures. In particular, most prior known tipping agents, other than cyanoacrylate, do not adhere well to lubricant coated sutures, which may result in inconsistent tipping or an undesirable reduction of suture-needle pull out force. The melt fusing method of tipping may destroy the lubricant coating or render it less effective in areas away from the needle.

Although tipped sutures prepared in accordance with the above procedures have been used successfully, there are several drawbacks with the use of tipping solutions. The main problems relate to tipping consistency and process control. Non-uniform solvent evaporation, which may be caused by variations in the solvent, oven temperature and heating time can result in inconsistent tipping. Furthermore, the dried residue of polymer left after evaporation can flake off or develop cracks. Additionally, an excess length of suture must be tipped to provide a sufficient length of stiff suture for handling during insertion into the needle. However, this undesirably results in a stiff suture segment adjacent the needle.

Therefore, it would be desirable to provide a method of treating a suture portion to provide a non-brooming suture tip for insertion into the bore of a needle. Further, it would be desirable to provide a reversibly tipped suture such that the suture tip is sufficiently stiff and non-brooming to be inserted into a needle bore but which does not result in a stiff suture segment adjacent the needle after attachment of the suture to the needle. Still further, it would be desirable to provide a suture tipping method which may be used with a variety of suture materials, either coated or uncoated.

SUMMARY OF THE DISCLOSURE

In accordance with the preferred method a delimited portion of the suture is immersed into a freezing media such as liquid nitrogen. After the delimited portion is frozen, the delimited portion is cut while in the frozen state to provide a stiffened, non-brooming suture tip. Preferably, the frozen suture section is cut while still immersed in the freezing media. The frozen, cut suture tip is inserted into a needle bore and the needle is crimped to attach the suture to the needle. As the needle-suture combination returns to ambient temperature, the freezing of the suture tip is reversed, and the suture portion adjacent the needle advantageously returns to the same flexibility as the remainder of the suture.

An apparatus for freezing the suture delimited portion includes at least one suture gripping arm to hold the suture during immersion of the delimited portion into the freezing media, a vessel containing the freezing media, and a cutting apparatus to cut the frozen suture delimited portion. Preferably, a pair of arms hold the suture at spaced apart locations to define the delimited portion, with both arms being immersed into the vessel and the cutting member cutting the suture between the arms. The apparatus may be combined with an apparatus for feeding suture material and may further be combined with a apparatus for automatically inserting the suture tip into a needle and crimping the needle to attach the suture to the needle and form a needle-suture combination.

DETAILED DESCRIPTION OF PREFERRED EMBODIMENT(S)

Figure 1:
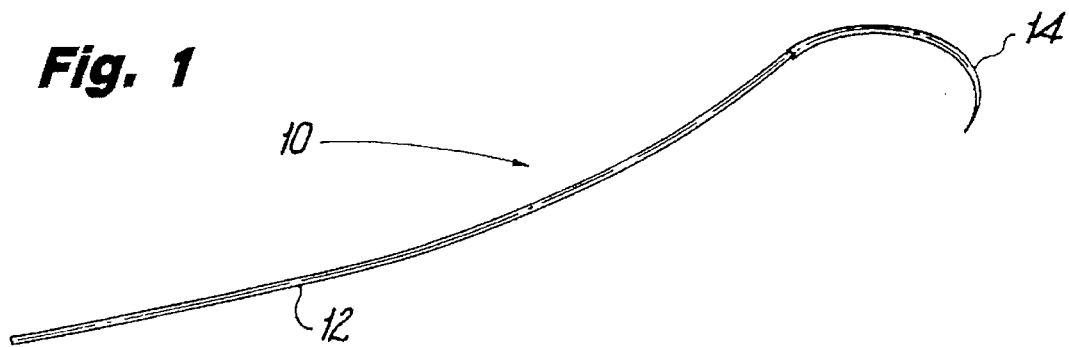
FIG. 1 is a perspective view of a needle suture combination.

The present disclosure is directed to a method, apparatus and system for tipping and cutting multifilament sutures, especially braided sutures, and to the insertion of the cut, tipped suture into a needle for attachment of the suture to a needle. The term "braid" means a substantially symmetrical strand formed by crossing a number (at least three) of individual strands composed of one or more filaments diagonally in such manner that each strand passes alternatively over and under one or more of the others. The braid may be of traditional tubular braid construction or spiroid braid construction and may include a core section composed of one or more filaments around which the braid is externally fabricated. See, e.g., U.S. Pat. Nos. 3,187,752; 3,565,077; 5,019,093; 5,059,213; and 5,261,886.

The braided suture can be fabricated from a wide variety of natural and synthetic fibrous materials. Such materials include non-absorbable as well as partially and fully bio-absorbable (i.e., resorbable) natural and synthetic fiber-forming polymers. Non-absorbable materials which are suitable for fabricating braided sutures include silk, polyamides, polyesters such as polyethylene, polypropylene, silk, cotton, linen, etc. Carbon fibers, steel fibers and other biologically acceptable inorganic fibrous materials can also be employed. Bio-absorbable sutures may be fabricated from natural collagenous material or synthetic resins including those derived from glycolic acid, glycolide, lactic acid, lactide, dioxanone, polycaprolactone, epsilon-caprolactone, trimethylene carbonate, etc., and various combinations of these and related monomers. Sutures prepared from resins of this type are known in the art. See e.g. U.S. Pat. Nos. 3,297,033; 3,839,297; and 4,429,080.

Braided multifilament sutures typically are coated with one or more coating compositions to improve functional properties such as surface lubricity and knot tie-down behavior. A variety of suture coating compositions proposed for either or both of these purposes are well known in the art. See, e.g., those disclosed in U.S. Pat. Nos. 3,867,190; 3,942,532; 4,047,533; 4,452,973; 4,624,256; 4,649,920; 4,716,203; 4,826,945; 4,994,074; 5,123,912; and 5,312,437.

Absorbable braided sutures may also contain a storage stabilizing amount of a filler material containing at least one water soluble liquid polyhydroxy compound and/or ester thereof. In addition to having an enhanced degree of storage stability, a braided suture which has been filled with a storage stabilizing amount of, e.g., glycerol, exhibits better flexibility and "hand" characteristics than the untreated suture. Moreover, since the polyhydroxy compounds are generally capable of dissolving a variety of medico-surgically useful substances such as therapeutic agents, they can be used as vehicles to deliver such substances to a wound or surgical site at the time the suture is introduced into the body. Therapeutic agents can be chosen for antimicrobial properties, capability for promoting wound repair and/or tissue growth or for specific indications such as thrombosis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a surgical or trauma wound site. To promote wound repair and/or tissue growth, one or more biologically active materials known to achieve either or both of these objectives can be applied to the braided suture of the present invention. Such materials include any of several Human Growth Factors (HGFs), magainin, tissue or kidney plasminogen activator to cause thrombosis, superoxide dismutase to scavenge tissue damaging free radicals, tumor necrosis factor for cancer therapy, colony stimulating factor, interferon, interleukin-2 or other lymphokine to enhance the immune system, and so forth. Filling compositions suitable for use as a storage stabilizing agent and for delivery of medico-surgically useful substances such as therapeutic agents are disclosed in U.S. Pat. Nos. 5,037,429 and 5,051,272.

Referring now to the drawings, FIG. 1 shows a needle-suture combination 10 having a length of suture attached to a needle 14. The present disclosure relates to treatment of a portion of the suture to provide a suitable suture tip for insertion into a bore for attachment to a needle.

Figure 2:
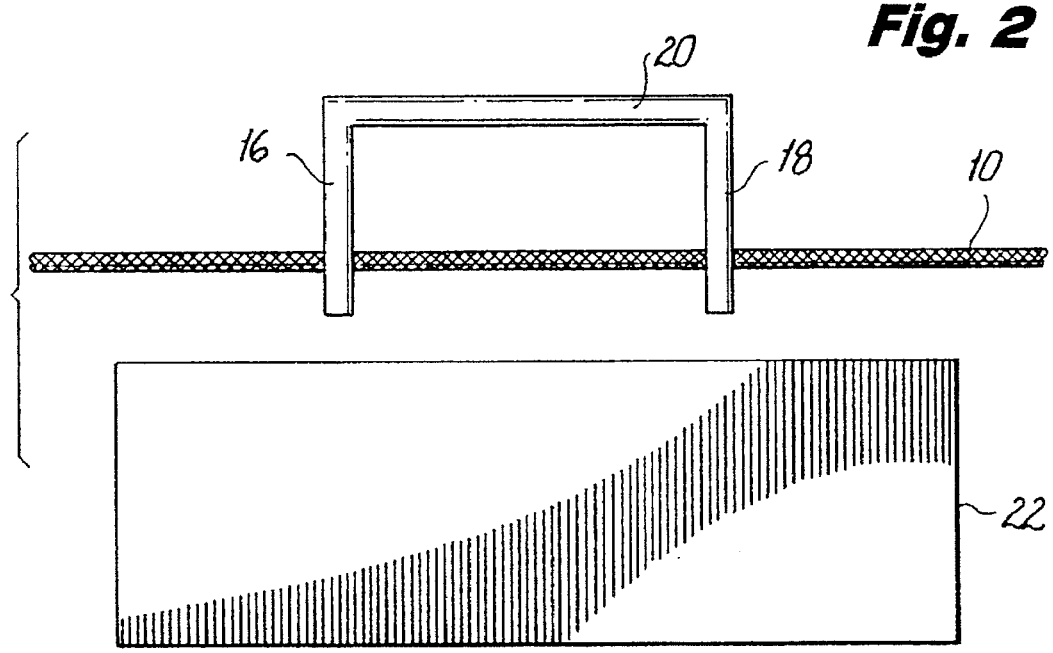
FIG. 2 is an elevation view of a suture portion selected for treatment, schematically illustrating the suture positioned for insertion into a treatment vessel.

FIG. 2 schematically illustrates a running length of suture 10 grasped by a pair of arms 16, 18 with a section of the suture extending between the arms. As shown in FIG. 2, arms 16, 18 may be mounted to a common support 20 connecting the two which, in turn is supported by a frame (not shown). Of course, the arms also could be mounted independently of one another. It is also contemplated that only one arm might be used, and that more than two arms could be used. Each arm preferably is provided with a jaw for grasping the suture with sufficient pressure to firmly hold the suture and prevent slippage through the jaw, while not damaging the suture. Suitable jaws may have rubber or metal grips, or grips of any other material not subject to degradation or having deleterious effects upon the suture when the grips and suture are frozen as described below. In FIG. 2, arms 16, 18 gripping suture 10 are positioned above a vessel 22 containing a media for freezing the suture. Preferably, the media is liquid nitrogen, although other media capable of freezing the suture without causing deleterious effects on the suture may be used, if desired.

Figure 3:
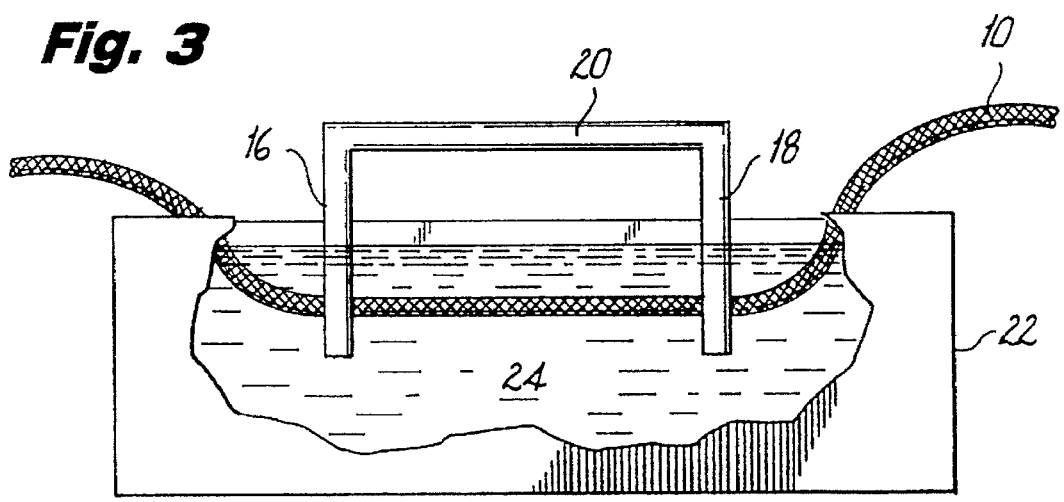
FIG. 3 is an elevation view, in partial cross-section, schematically illustrating the selected suture portion inserted into the treatment vessel.
Figure 4:
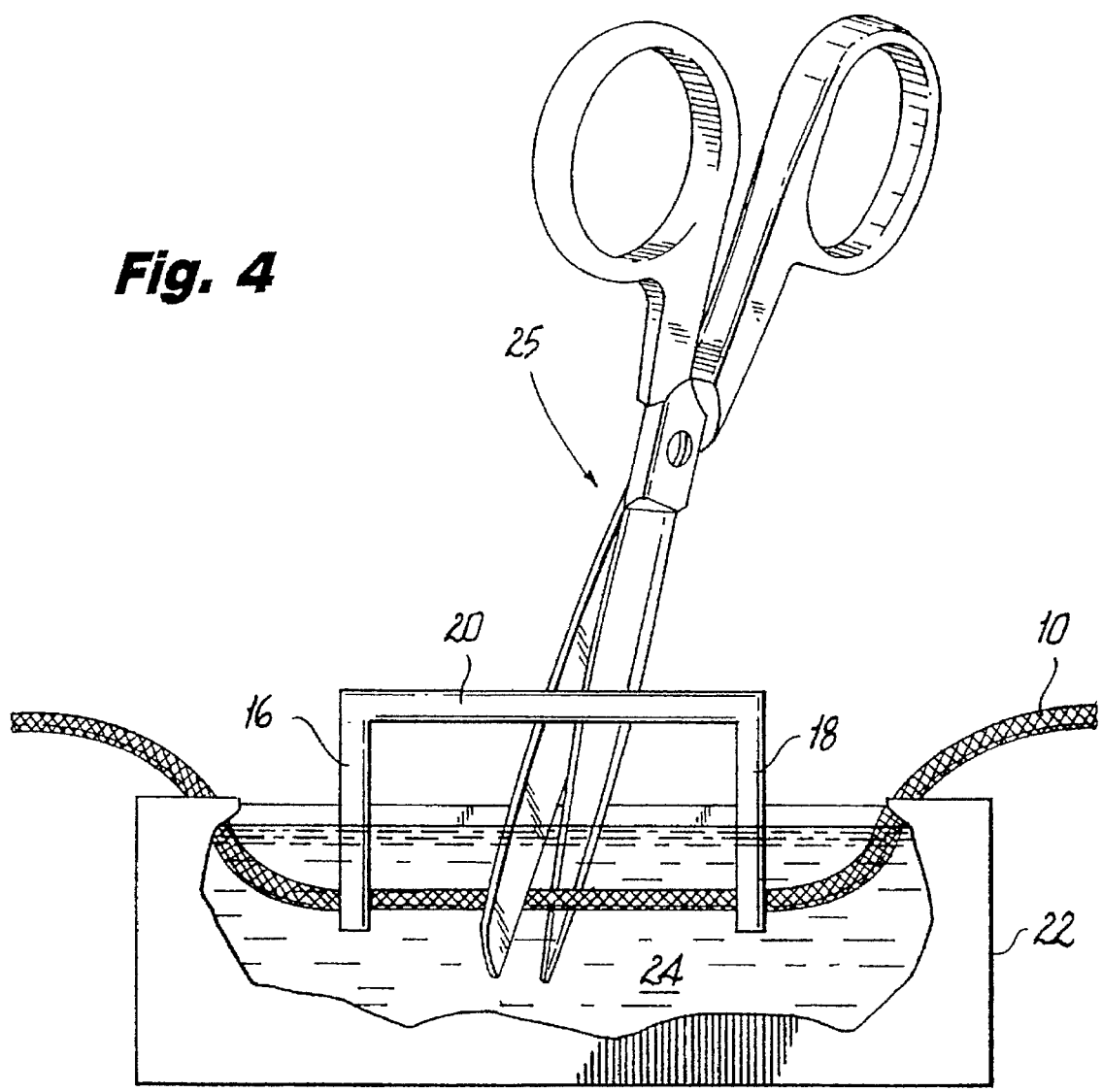
FIG. 4 is an elevation view, in partial cross-section, schematically illustrating the treated suture portion being cut while in the treatment vessel.

FIG. 3 is a partial cross-section schematic view of vessel 22 with the gripping arms and suture immersed into a freezing media 24. The freezing media may be any media which has a sufficiently low temperature to freeze the suture material so the suture filaments become stiff and will not separate upon being cut until the suture is warmed to ambient temperature. The preferred freezing media is liquid nitrogen, but other media such as liquid helium, liquid oxygen, etc. may be suitable. As shown, the portion of suture 10 between arms 16, 18 is placed into the freezing media, with the ends of the suture leading out of the vessel to the remainder of the suture not being treated. In FIG. 4, a pair of sharp scissors 25 have been inserted into the vessel to cut the frozen suture between arms 16, 18.

The method of the disclosure includes the steps of delimiting a portion of the suture to be treated, exposing the delimited suture portion to a freezing media, and cutting the frozen suture portion to provide a frozen cut suture tip. The frozen cut tip does not broom and remains stiff, facilitating insertion of the suture tip into the bore of a needle. The preferred mode of delimiting a portion of the suture is to grip the suture between two arms, but any variety of ways of delimiting the suture will work satisfactorily, such as manually grasping the suture with one or more forceps to manually insert the suture portion into the freezing vessel. Similarly, while scissors to cut the frozen suture are shown for purposes of illustration, it is contemplated that linear or rotary blades could be used, such as a razor blade. Preferably, the frozen suture is cut while the suture portion is immersed in the freezing media in order to prevent warming effects of the cutting apparatus on the frozen suture. Of course, satisfactory results may be achieved by cooling the cutting blade(s) so that the suture may be cut after the suture has been removed from the vessel, or by other methods of preventing against premature warming of the suture.

When liquid nitrogen is used as the freezing media the suture portion is frozen almost immediately upon insertion into the vessel, although the time required to freeze the suture portion may depend in part upon the time required to lower the temperature of surrounding structures such as the gripping ends. Preferably, however, the suture portion is immersed into the freezing media for several seconds to assure complete, uniform freezing of the suture portion. Most preferably, the suture portion is immersed into the freezing media for at least 5 seconds. As stated, it also is preferred to cut the suture in the freezing media with a blade or other cutting apparatus which has been immersed into the freezing media and, therefore, is at substantially the same temperature as the frozen suture.

Figure 5:
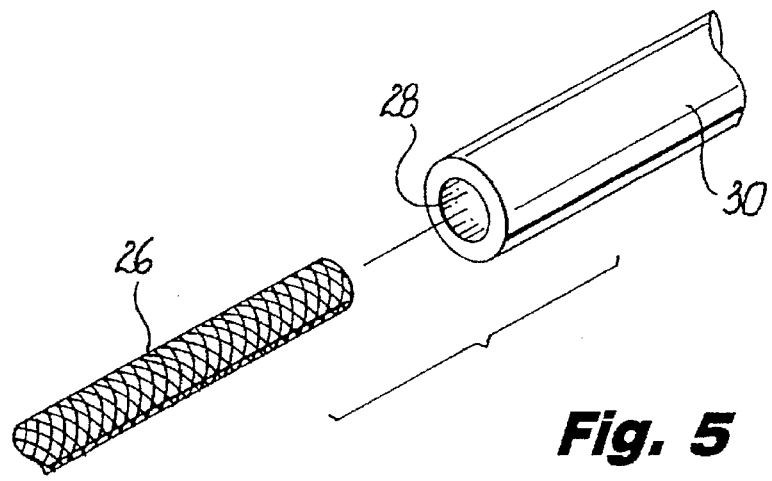
FIG. 5 is a partial perspective view illustrating the treated suture tip being inserted into the bore of a needle for attachment thereto.

After the cut suture is removed from the freezing media, the cut, frozen suture tip is stiff and does not broom. Thus, the suture tip is suitable for insertion into a needle bore. Referring to FIG. 5, the cut, frozen suture tip 26 is inserted into bore 28 of the blunt end 30 of needle 14. Because the suture filaments are frozen in place, the filaments do not spread and the suture tip may readily be inserted into the needle. In addition, because the frozen suture filaments are stiff, the tip of the suture is readily directed into the needle bore. Preferably, the cut, frozen suture tip is inserted into the needle bore within a few seconds of removal of the suture tip from the freezing media in order to avoid warming which reverses the stiffening effect of freezing the suture. Preferably, the suture tip is inserted into the needle in less than 5 seconds after removal from the freezing media. Most preferably, the suture tip is inserted into the needle within about 2 seconds after removal from the freezing media. Thereafter, the end of the needle may be crimped in a known manner to attach the suture to the needle.

The presence of a freezable substance in or on the suture will promote the stiffening effects of freezing the suture portion. Synthetic absorbable sutures have a natural tendency to attract moisture, and the moisture so attracted during handling and processing renders the process disclosed herein particularly useful with respect to synthetic absorbable sutures. The effects of the freezing process may be promoted by applying a freezable substance, such as moisture, to the suture. Thus, with all types of sutures the process may be promoted, for example, by humidifying the suture delimited portion prior to freezing. The humidifying effect may be localized to the delimited portion or may simply consist of humidifying the ambient conditions of the environment in which the process is performed.

Advantageously, the freezing effect upon the suture is fully reversible upon warming of the suture to room temperature. Thus, after the needle-suture attachment is complete, the suture returns to room temperature and the portion of the suture adjacent the needle is of the same flexibility as the remainder of the suture. Conventional tipping methods such as heat fusing and adhesive tipping result in a length of suture adjacent the needle which is stiff. Surgeons find a stiff suture segment adjacent the needle undesirable, so the ability to provide a needle-suture attachment without this undesirable feature is an important advantage.

As a further advantage of the method of treating a suture and the resulting needle-suture combination, the method may be utilized with all types of suture materials with or without coatings, fillers or therapeutic agents. Advantageously, any moisture associated with coatings or fillers promotes the stiffening effect caused by freezing the suture. Unlike melt fusing, the present method does not weaken the suture filaments or destroy therapeutic agents such as growth factors. To the contrary, freezing is quite compatible with handling and delivery of growth factors.

While the above description contains may specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto. By way of example only, it is contemplated that the process could be automated, with the suture automatically being advanced for treatment, selectively frozen, cut, and inserted into the needle. In this regard, the apparatus of U.S. patent application Ser. No. 08/309,705, hereby incorporated by reference, may be used to advance the suture material for freezing and cutting, and for insertion into the needle. As to the latter, the tip of the cut, tipped suture could be inserted directly into a needle attachment apparatus, such as the apparatus of U.S. patent application Ser. Nos. 07/959,114 and 08/100,716, both of which are hereby incorporated by reference. It further is contemplated that the suture tip may be inserted into a channeled needle, or into a shrinkable tube to be attached to a needle shank by swaging or heat treatment.

As used in the appended claims, the term "delimiting means" is intended to refer to one or more graspers or gripping arms to hold the suture for immersion into the freezing media, and equivalent structures.

As used in the appended claims, the term "freezing means" is intended to refer to a media suitable for lowering the temperature of the suture portion sufficiently to stiffen the treated suture portion, including liquid nitrogen and equivalent low temperature media.

As used in the appended claims, the term "cutting means" is intended to refer to a cutting apparatus suitable for cutting the frozen suture portion, including scissors, a razor blade, one or more linear or rotary cutting blades, and equivalent structures.

What is claimed is:

1. A system for treating a multifilament suture which comprises:
    a) a pair of arms defining a delimited portion of the multifilament suture extending therebetween;
    b) freezing means for freezing the delimited portion;
    c) cutting means for cutting the delimiting portion while the delimited portion is in a frozen state to provide a frozen suture tip suitable for insertion into a needle bore.

2. The system of claim 1 wherein the freezing means comprise liquid nitrogen.

3. The system of claim 1 wherein the cutting means are selected from the group consisting of scissors, a knife, a rotary blade, and a razor knife.

* * * * *